(12) United States Patent
Kupferstein

(10) Patent No.: US 9,775,734 B1
(45) Date of Patent: Oct. 3, 2017

(54) HAND SUPPORT METHOD AND DEVICE FOR SOMATOSENSORY INPUT TO THE PALM

(71) Applicant: Doogri, Inc., Alameda, CA (US)

(72) Inventor: Henny Kupferstein, Alameda, CA (US)

(73) Assignee: Doogri, Inc., Alameda, CA (US)

( * ) Notice: Subject to any disclaimer, the term of this patent is extended or adjusted under 35 U.S.C. 154(b) by 0 days.

(21) Appl. No.: 15/201,483

(22) Filed: Jul. 3, 2016

(51) Int. Cl.
*B68G 5/00* (2006.01)
*A61F 4/00* (2006.01)

(52) U.S. Cl.
CPC ....................... *A61F 4/00* (2013.01)

(58) Field of Classification Search
CPC ... A61G 13/10; B25B 1/08; F16B 2/14; F16B 2/18; A45D 2029/045
USPC .... 248/118, 226.11, 231.31, 231.71, 231.61, 248/229.21, 229.11, 228.2, 230.2; 132/73, 73.5
See application file for complete search history.

(56) References Cited

U.S. PATENT DOCUMENTS

| | | | | |
|---|---|---|---|---|
| 2,171,804 A | * | 9/1939 | Fernando | A45D 29/22 |
| | | | | 132/73 |
| 4,615,522 A | | 10/1986 | Plough | 272/67 |
| 5,086,762 A | | 2/1992 | Chee | 602/4 |
| 5,184,795 A | * | 2/1993 | Sexton | A45D 29/22 |
| | | | | 132/73 |
| 5,638,831 A | | 6/1997 | Brown | 128/898 |
| 6,447,464 B1 | | 9/2002 | Dunlevy et al. | 601/40 |
| 6,769,657 B1 | * | 8/2004 | Huang | F16M 11/10 |
| | | | | 248/278.1 |
| 8,763,297 B2 | * | 7/2014 | Boll | A01M 31/02 |
| | | | | 42/94 |

(Continued)

FOREIGN PATENT DOCUMENTS

| | | |
|---|---|---|
| CN | 101303804 | 6/2008 |
| CN | 201266442 | 10/2008 |

(Continued)

OTHER PUBLICATIONS

Henny Kupferstein and Bong Walsh, "Non-Verbal Paradigm for Assessing Individuals for Absolute Pitch", World Futures, 0: Jan. 16, 2015.

*Primary Examiner* — Steven Marsh
(74) *Attorney, Agent, or Firm* — Imperium Patent Works; Amir V. Adibi

(57) ABSTRACT

A hand support device and method for somatosensory input to the palm comprises a support portion and an attachment portion. The support portion forms a rounded surface that supports a hand of a user. The attachment portion attaches to a structure. The device activates purposeful motor movement with accurate motor control for users with Dyspraxia when employed in conjunction with evidence-based developmental pedagogy in high stimulating tasks such as music education per the Rancer Method (Kupferstein & Walsh, 2015). In one example, the hand support device attaches to a piano and clamps to the keyslip allowing the user to rest their hand while playing the piano. In another example, the hand support device is adapted to attach to a surface of a laptop or desk with a base surface that is disposed above the laptop, allowing the user to rest their hand while typing on the keyboard.

20 Claims, 15 Drawing Sheets

SIDE VIEW OF HAND SUPPORT DEVICE
(FIRST EMBODIMENT)

(56) References Cited

U.S. PATENT DOCUMENTS

| | | | |
|---|---|---|---|
| 9,038,971 B1* | 5/2015 | Guthrie | F16M 13/022 248/121 |
| 2006/0005296 A1 | 1/2006 | Moore | 2/159 |
| 2017/0006994 A1* | 1/2017 | King | A45D 29/00 |

FOREIGN PATENT DOCUMENTS

| | | |
|---|---|---|
| CN | 202512756 | 4/2012 |
| CN | 203706655 | 2/2014 |
| CN | 203773778 | 3/2014 |

* cited by examiner

SIDE VIEW OF HAND SUPPORT DEVICE
(FIRST EMBODIMENT)

PERSPECTIVE VIEW OF HAND SUPPORT DEVICE

PERSPECTIVE VIEW OF HAND SUPPORT DEVICE

FRONT VIEW OF HAND
SUPPORT DEVICE

BACK VIEW OF HAND
SUPPORT DEVICE

TOP VIEW OF HAND SUPPORT DEVICE

BOTTOM VIEW OF HAND SUPPORT DEVICE

HAND SUPPORT DEVICE

SIDE VIEW OF HAND SUPPORT DEVICE
FOR SMALLER HANDS
(SECOND EMBODIMENT)

SIDE VIEW OF HAND SUPPORT DEVICE
(THIRD EMBODIMENT)

PACKAGED HAND SUPPORT DEVICE

AMOUNT OF INSTRUCTIONS

HAND SUPPORT METHOD AND DEVICE FOR SOMATOSENSORY INPUT TO THE PALM

TECHNICAL FIELD

The described embodiments relate generally to support methods, and more particularly to hand support devices directed to motor control disorders.

BACKGROUND INFORMATION

Motor planning disorder is a condition often associated with dyspraxia, autism, and other neurodevelopment disorders. Motor planning dysfunction prevents a person from having accurate motor movements as compared to typically developed individuals. As a result, physical assistance is required from caregivers. Unfortunately, caregiver dependence may prevent people with dyspraxia from independently executing tasks that require fine and gross motor movements. Evidence based methodologies are desired to remediate these challenges.

SUMMARY

A hand support device comprises a support portion and an attachment portion. The support portion forms a rounded surface that supports a hand of a user. The attachment portion attaches to a structure, such as a piano or a laptop. The hand support device is adapted to be used for people with dyspraxia. When the hand is placed above the support portion, the weight of the hand causes the support portion to apply pressure onto a center of the palm. By applying specific pressure into the center of the palm, bones on the top of the hand shift to activate the muscles in between the hand bones, which are then available to receive signals from the brain to complete the motor plan. In this fashion, the applied force creates a synthetic shoulder for gross-to-fine translation. When independent finger isolations emerge, the need for the applied force will subside. In accordance with one novel aspect, neuroplastic changes in the motor systems of the user with dyspraxia will habituate movement through muscle memory for the completion of complex tasks such as playing the piano or typing on a keyboard without needing the hand support device.

In one embodiment, the hand support device is adapted to attach to a piano. The attachment portion of the device has a clamping mechanism that clamps onto the ledge of the piano keyslip allowing the user to rest their hand on the device while playing the piano. The clamping mechanism has a tail having a hole, a fastening element that extends through the hole, and a ledge that extends downward from the base of the support portion. A user attaches the clamping mechanism to the keyslip of the piano and tightens the fastening element until the hand support device is securely attached to the piano. The attachment portion contacts the structure along at least three surfaces. Next, the user places his/her hand above the hand support device and may play the piano keys with his/her fingers.

In another embodiment, the hand support device is adapted to attach to a surface of a laptop or desk. The attachment portion of the device has a base that has a planar surface. The planar surface is adapted to be disposed above a flat surface of a structure. A user places the support device above the laptop surface below the keyboard. The attachment portion contacts the structure at a single surface. Next, the user places his/her hand above the hand support device and may type on the keyboard with his/her fingers.

The foregoing is a summary and thus contains, by necessity, simplifications, generalizations and omissions of detail; consequently it is appreciated that the summary is illustrative only. Still other methods, and structures and details are set forth in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

Reference will now be made in detail to some embodiments of the invention, examples of which are illustrated in the accompanying drawings.

DETAILED DESCRIPTION

Figure 1:
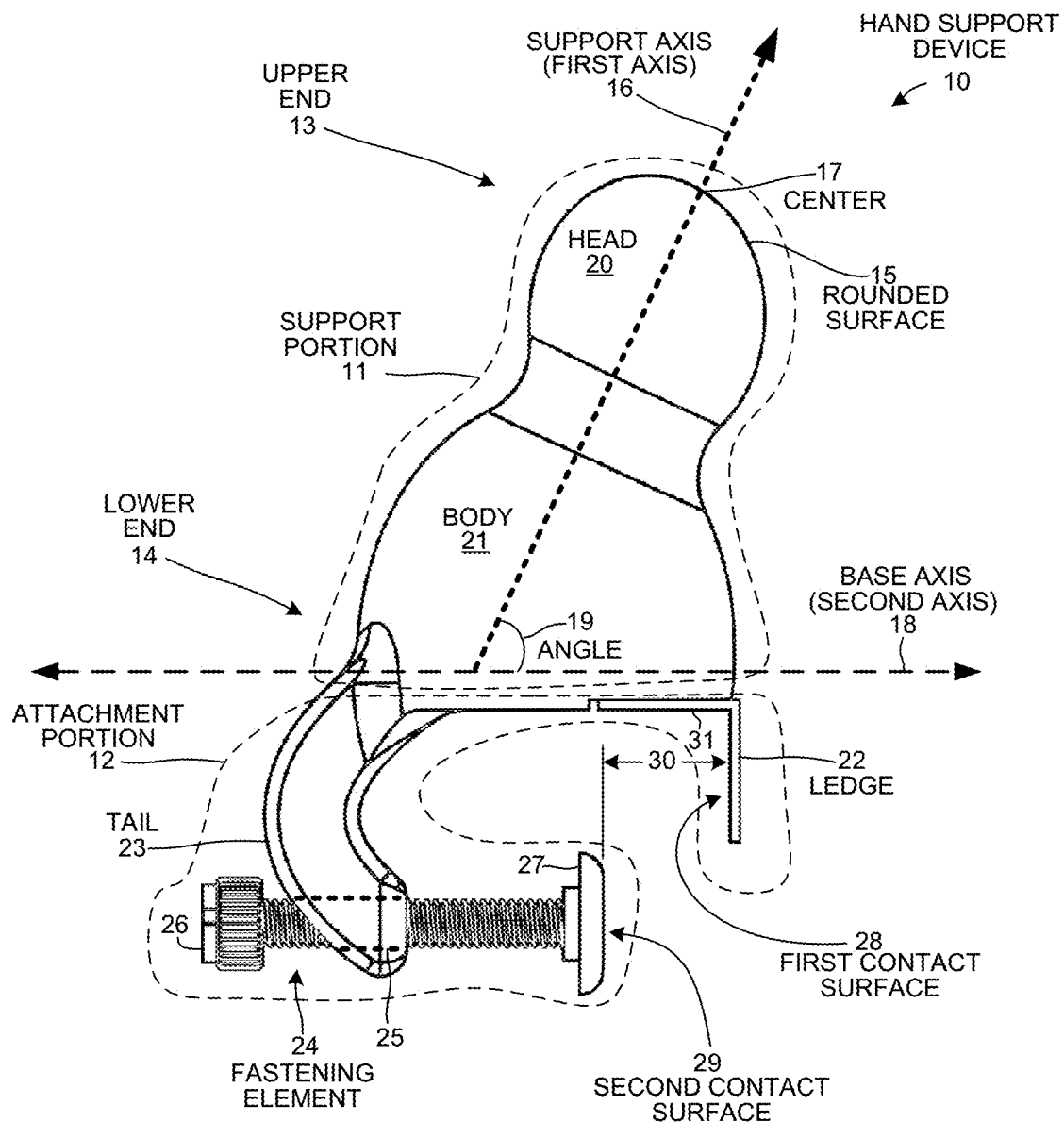
FIG. 1 is a diagram of a hand support device 10.

FIG. 1 is a diagram of a hand support device 10. The hand support device 10 comprises a support portion 11 and an attachment portion 12. The support portion 10 has an upper end 13 and a lower end 14. The upper end 13 forms a rounded surface 15. The rounded surface 15 is adapted to receive a palm of a hand, for example, the hand of a piano student with dyspraxia. The support portion 11 extends from the lower end 14 to the upper end 13 along a first axis 16. The first axis 16 is a support axis and extends through a center 17 of the rounded surface 15. The first axis 16 is normal to the center 17. A second axis 18 is disposed along the lower end 14 of the support portion 11. The second axis 18 is a base axis. The first axis 16 forms an angle 19 relative to the second axis 18. The angle 19 between the first axis 16 and the second axis 18 is between twenty degrees (20°) and ninety degrees (90°). Typically, the angle 19 is approximately forty five degrees (45°). The attachment portion 12 has a head 20 and a body 21.

The attachment portion 12 is connected to the lower end 14 of the support portion 12. In the example of FIG. 1, the attachment portion 12 comprises a clamping mechanism having a ledge 22, a tail 23, and a fastening element 24. The clamping mechanism is adapted to attach to a piano such that a student with dyspraxia can play independent of assistance from another person. The tail 23 forms a hole 25 through which the fastening element 24 extends. The fastening element 24 has a knob 26 and a tip 27. The ledge 22 includes a first contact surface 28. The tip 27 forms a second contact surface 29. When attaching the attachment mechanism to a structure, such as a piano, the first contact surface 28 is adapted to contact a first surface of the structure and the second contact surface 29 is adapted to contact a second surface of the structure.

In accordance with one novel aspect, the distance 30 between the first contact surface and the second contact surface is adjustable. To attach the hand support device 10 to a piano, a user inserts the ledge 22 into the keyslip 35 of the piano. Next, the user tightens the fastening element until the tip 27 and ledge 22 clamp the hand support device 10 onto the piano keyslip such that the hand support device 10 is stable. The user can rest his/her hand onto the rounded surface 15 of the head 20 and begin piano playing.

Figure 2:
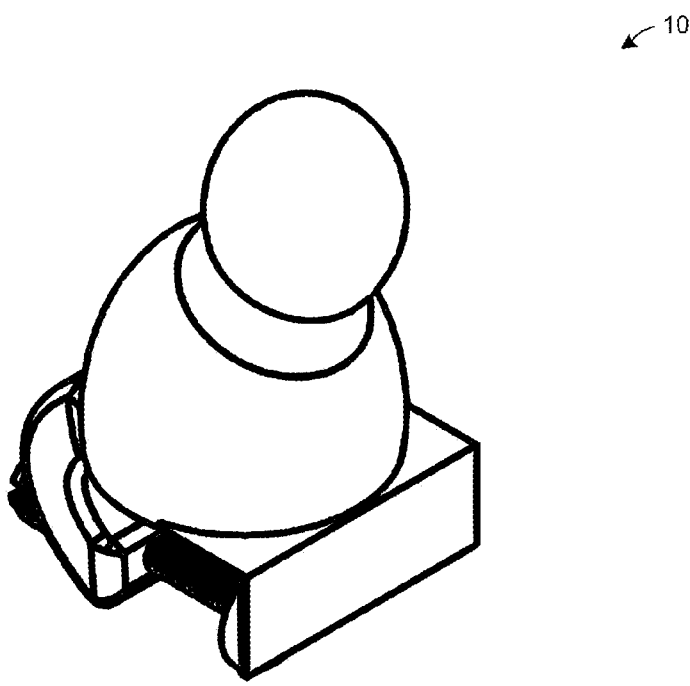
FIG. 2 is a diagram of a perspective view of the novel hand support device 10.

FIG. 2 is a diagram of a perspective view of the novel hand support device 10. The novel hand support device 10 is a unitary structure, except that the ledge 22 and fastening element 24 are separate structures attached to the device 10. The unitary structure is formed by an injection molding process. In another example, the hand support device 10 is printed from thermoplastic polymer material, such as acrylonitrile butadiene styrene (ABS), plastic resin materials, or other materials employed in 3D printing processes. In yet another example, the hand support device 10 is formed from metal, wood, glass, ceramic, or clay material. In yet another example, the hand support device is comprised of several components that are attached together to form the hand support device. For example, the head, body, and tail are each separate structures attached together via screws. The user receives the separate components and then assembles them together to form the hand support device.

Figure 3:
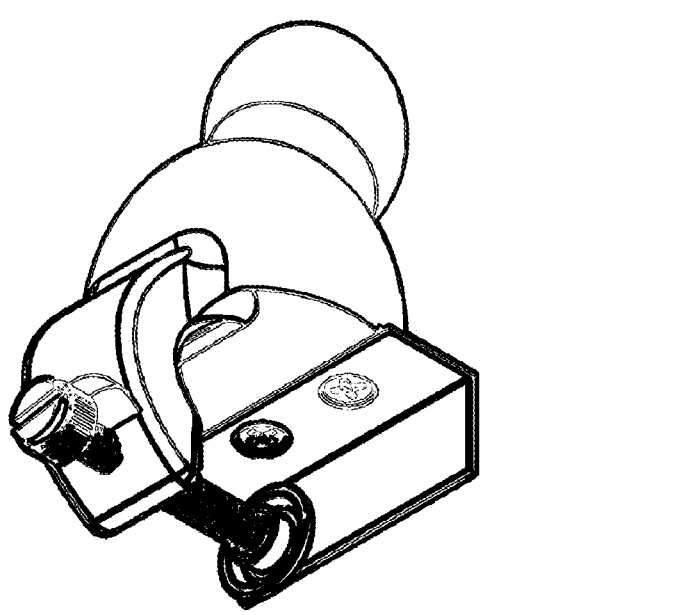
FIG. 3 is a diagram of another perspective view of the novel hand support device 10.

FIG. 3 is a diagram of another perspective view of the novel hand support device 10.

Figures 4, 5:
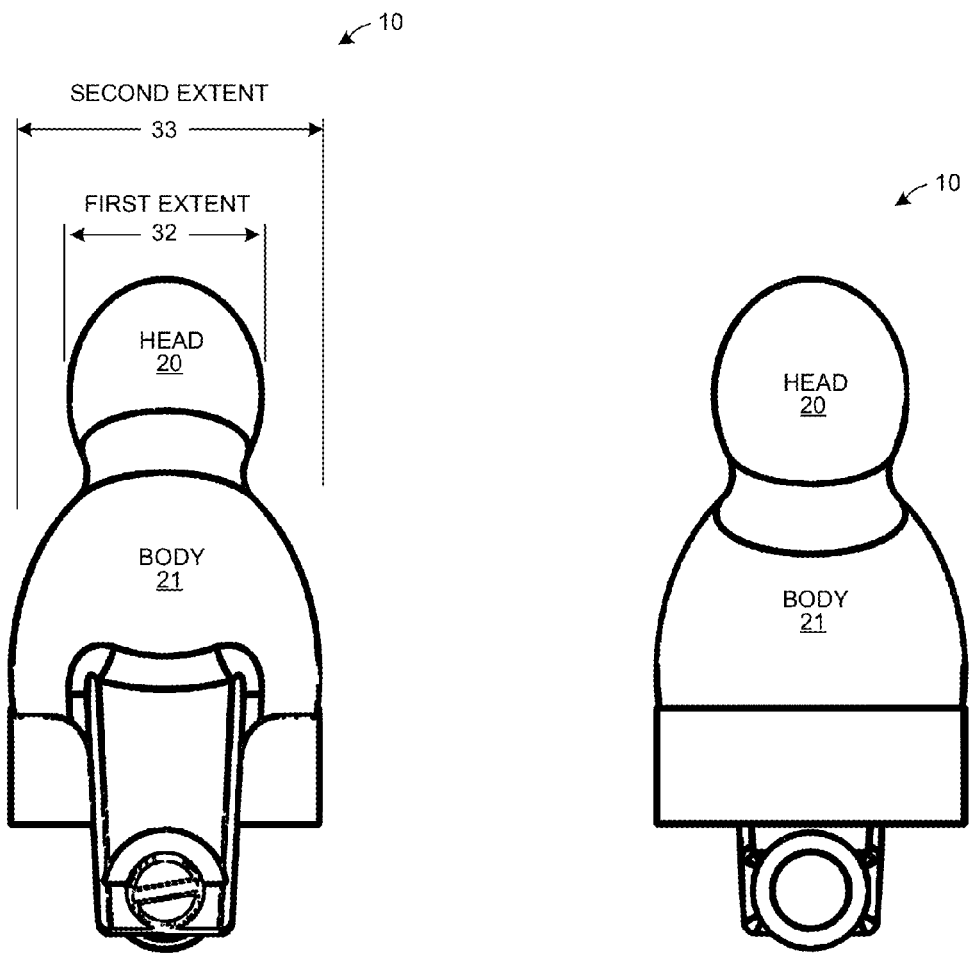
FIG. 4 is a diagram of a front perspective view of the novel hand support device 10.
FIG. 5 is a diagram of a back perspective view of the novel hand support device 10.

FIG. 4 is a diagram of a front perspective view of the novel hand support device 10. The head 20 has a first extent 32. The body 21 has a second extent 33. The second extent 33 is greater than or equal to the first extent 32. The first extent 32 is greater than half the length of the second extent 33. In another example, the first extent 32 is greater than the second extent 33. When the head and body of the device 10 have circular shapes when viewed from the top down perspective, as in this example, the first extent 32 and second extent 33 are also referred to as first and second diameters, respectively.

FIG. 5 is a diagram of a back perspective view of the novel hand support device 10.

Figure 6:
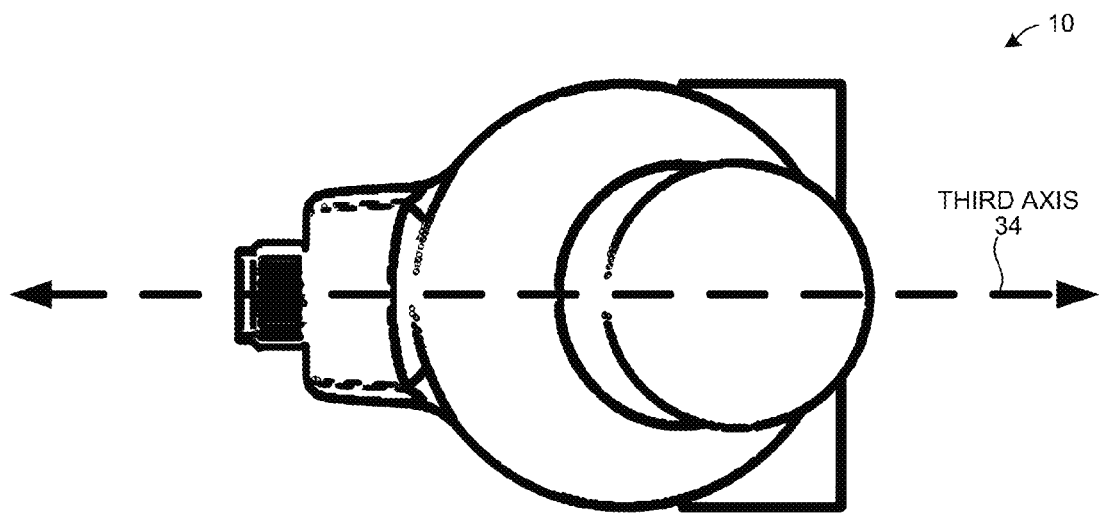
FIG. 6 is a diagram of a top perspective view of the novel hand support device 10.

FIG. 6 is a diagram of a top perspective view of the novel hand support device 10. A third axis 34 is shown. The support device 10 is symmetrical about the third axis 34.

Figure 7:
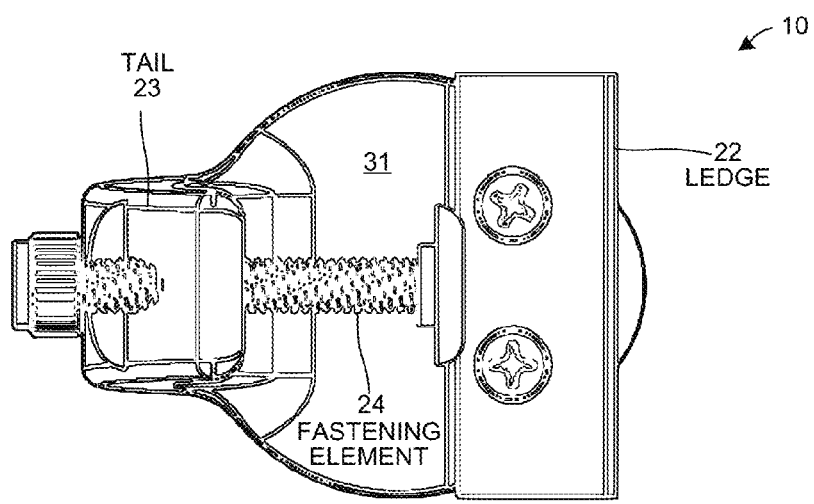
FIG. 7 is a diagram of a bottom perspective view of the novel hand support device 10.

FIG. 7 is a diagram of a bottom perspective view of the novel hand support device 10. The bottom surface 31 is adapted to rest upon at least one surface of the structure. The bottom surface 31 is a third contact surface of the device 10.

Figure 8:
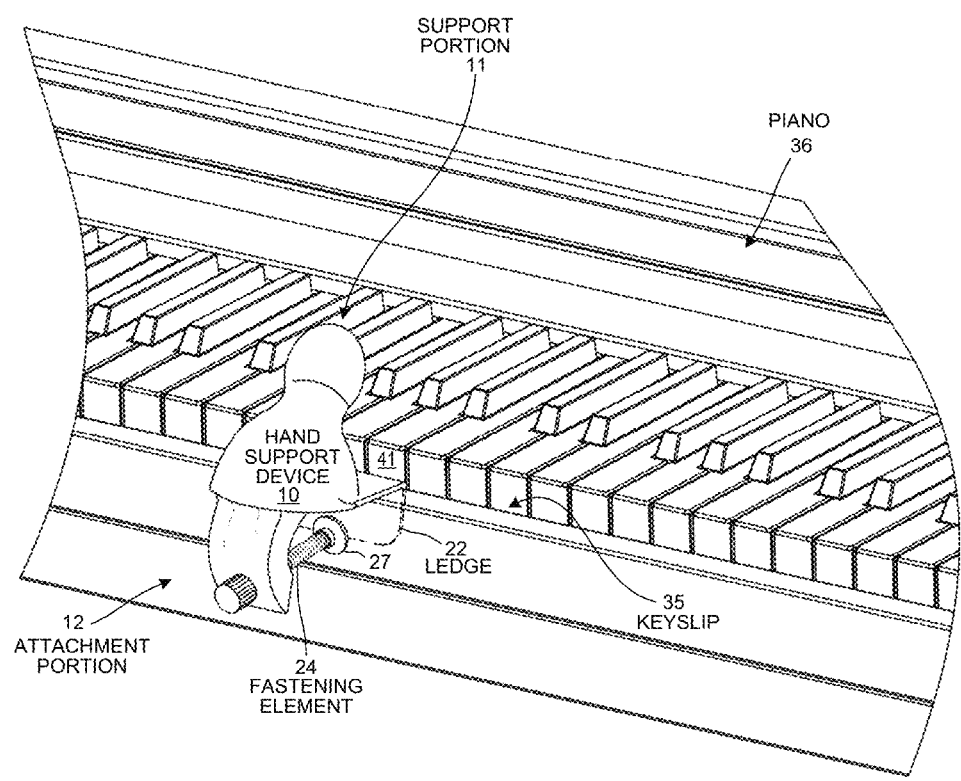
FIG. 8 is a diagram of a perspective view of the novel hand support device 10 attached to a keyslip 35 of a piano 36.

FIG. 8 is a diagram of a perspective view of the novel hand support device 10 attached to a keyslip 35 of a piano 36. The novel hand support device 10 contacts the keyslip 35 along at least three surfaces. The fastening element is tightened by the user so that the keyslip 35 is clamped between the tip 27 and ledge 22. In this fashion, the attachment portion 12 ensures that the hand support device 10 is held firmly in place along the keyslip 35 of the piano 36 so that a user may rest his/her hand on the support portion 11.

Figure 9:
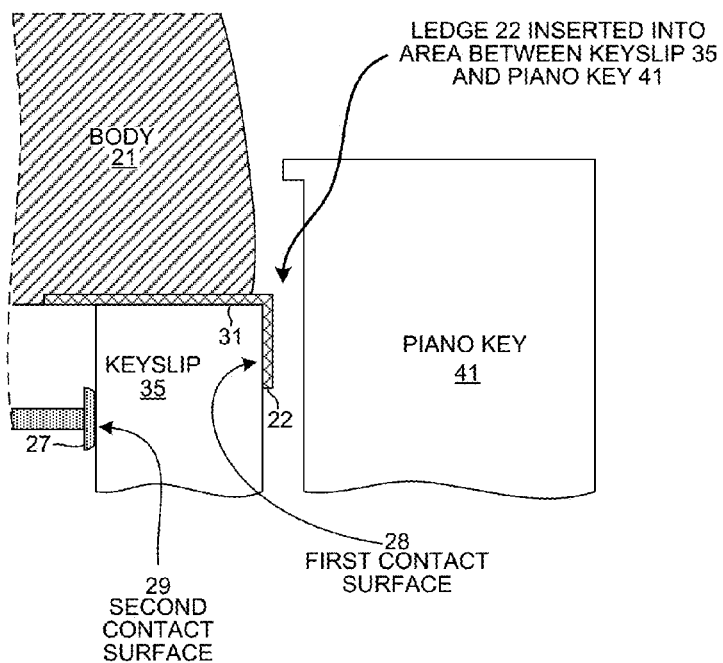
FIG. 9 is a diagram of a cross sectional view showing how the ledge 22 is inserted into the area between keyslip 35 and piano key 41.

FIG. 9 is a diagram of a cross sectional view showing how the ledge 22 is inserted into the area between keyslip 35 and piano key 41. The ledge 22 slides into the space between the keyslip 35 and key 41. The device 10 contacts the structure along at least three surfaces. For example, surfaces 28, 29, and 31 of device 10 contact keyslip 35 of the piano 36.

Figure 10:
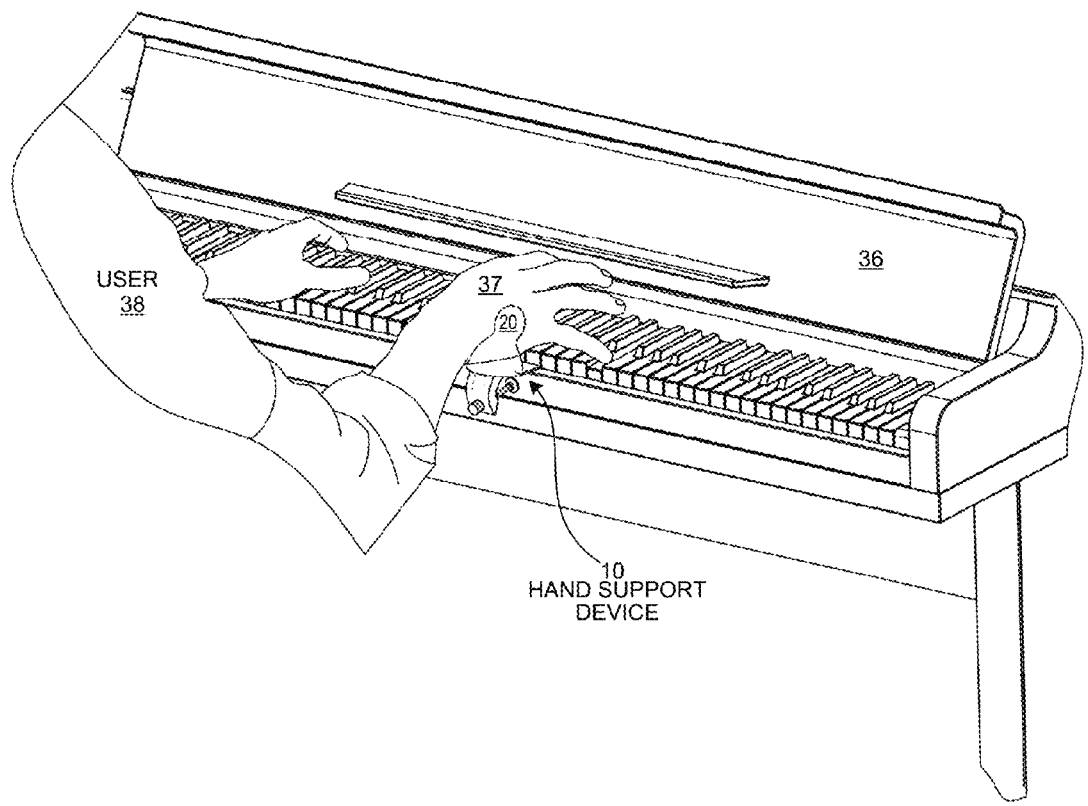
FIG. 10 is a diagram of a perspective view of the novel hand support device 10 supporting a hand 37 of a user 38.

FIG. 10 is a diagram of a perspective view of the novel hand support device 10 supporting a hand 37 of a user 38. The center of the palm rests on the head 20 of the hand support device 10. The hand support device 10 is attached to the piano 36 and allows the user 38 to play the piano 36 while the hand 37 is being supported by the hand support device 10.

Figure 11:
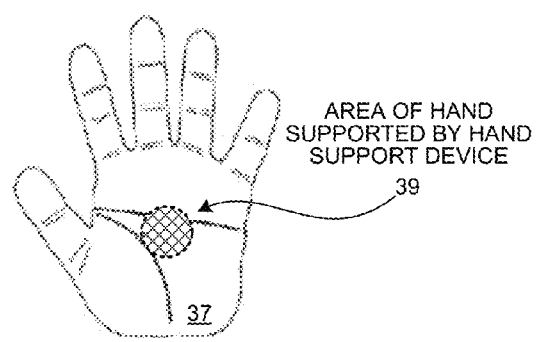
FIG. 11 is a diagram of a perspective view of the area 39 of the hand 37 that is supported by the novel hand support device 10.

FIG. 11 is a diagram of a perspective view of the area 39 of the hand 37 that is supported by the novel hand support device 10. An area 39 of the hand rests above the head 20 of the hand support device 10. The weight of the hand 37 above the head 20 causes an opposing force to be applied along area 39. By applying the force along area 39, a user 38 with dyspraxia is able to play the piano 36 under certain conditions.

Figure 12A:
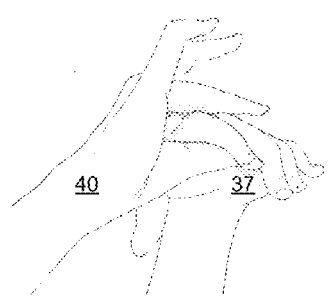
FIGS. 12A and 12B are diagrams showing perspective views of a caregiver 40 physically supplying somatosensory input to the area 39 of the hand 38.
Figure 12B:
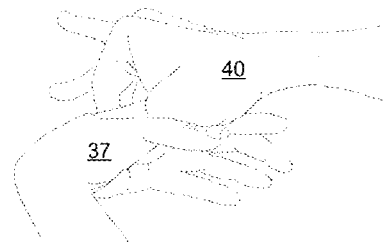

FIGS. 12A and 12B are diagrams showing perspective views of a caregiver 40 physically supplying somatosensory input to the area 39 of the hand 38. Without device 10, a caregiver may need to apply somatosensory input to the area 39 to augment the user's motor accuracy. The device 10 supplies substantially similar somatosensory input to area 39 to eliminate dependency on caregiver support.

Figure 13:
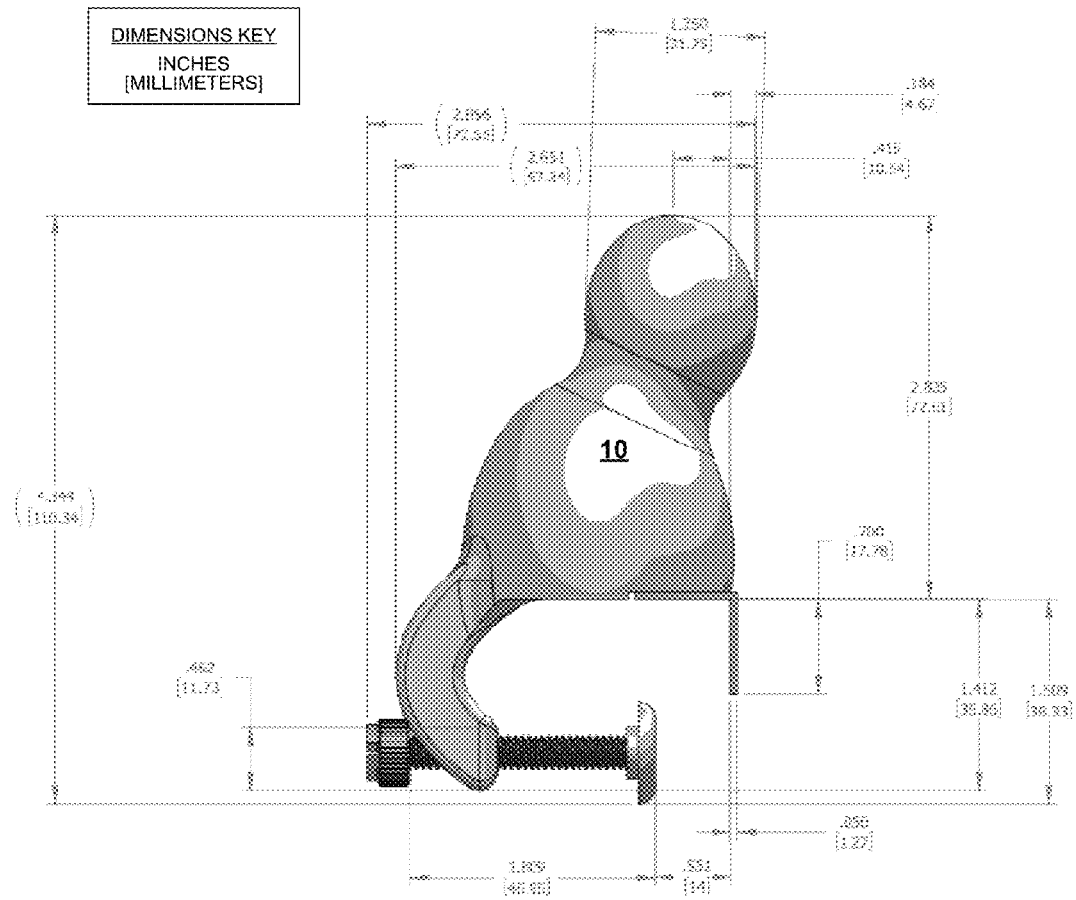
FIG. 13 is a diagram of a hand support device 10 showing the dimensions of one specific example along a side view.

FIG. 13 is a diagram of a hand support device 10 showing the dimensions of one specific example along a side view. The upper dimensions (not in brackets) are in inches. The lower dimensions (in brackets) are in millimeters. An artisan of ordinary skill will appreciate that the dimensions may vary according to the size of the hand or the size of the structure onto which the attachment portion is adapted to be attached to.

Figure 14:
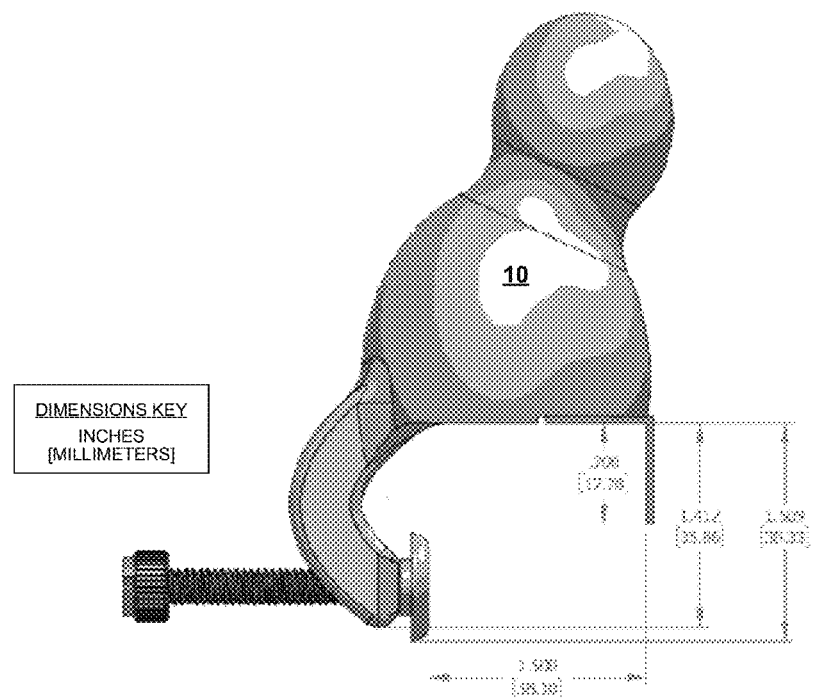
FIG. 14 is a diagram of a hand support device 10 showing the dimensions of the specific example along a side view when the fastening element is adjusted to allow for the maximum distance between the first and second contact surfaces.

FIG. 14 is a diagram of a hand support device 10 showing the dimensions of the specific example along a side view when the fastening element is adjusted to allow for the maximum distance between the first and second contact surfaces.

Figure 15:
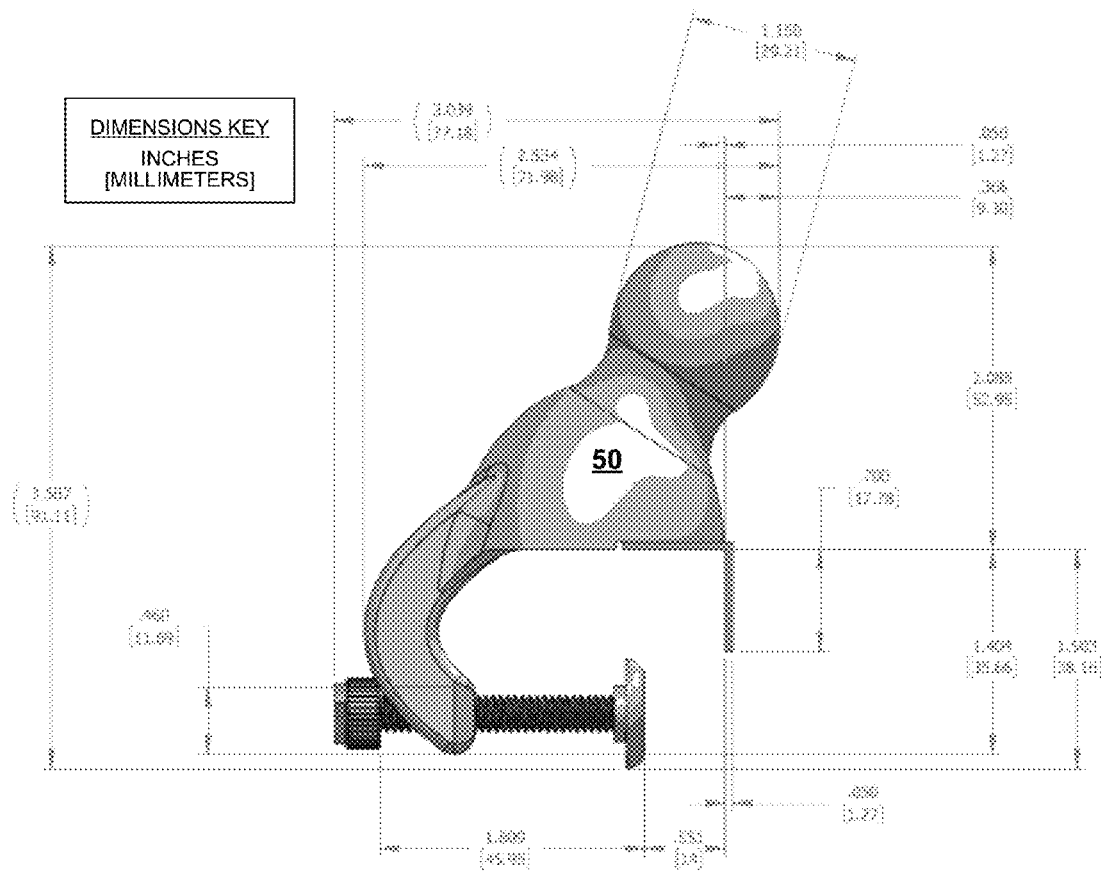
FIG. 15 is a diagram of a hand support device 50 showing the dimensions of another embodiment of a hand support device adapted for smaller hands.

FIG. 15 is a diagram of a hand support device 50 showing the dimensions of another embodiment of a hand support device adapted for smaller hands. The hand support device 50 has a head that is at a more acute angle with respect to the base axis. The hand support device 50 is suited for users with smaller hands, such as young children. The upper dimensions (not in brackets) are in inches. The lower dimensions (in brackets) are in millimeters. An artisan of ordinary skill will appreciate that the dimensions may vary according to the size of the hand or the size of the structure onto which the attachment portion is adapted to be attached to.

Figure 16:
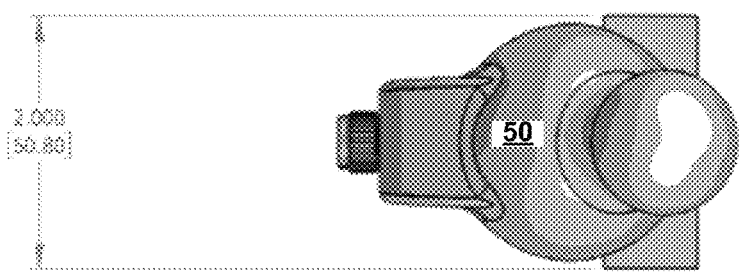
FIG. 16 is a diagram of a hand support device 50 showing additional dimensions of hand support device 50 from a top perspective view.

FIG. 16 is a diagram of a hand support device 50 showing additional dimensions of hand support device 50 from a top perspective view. The upper dimensions (not in brackets) are in inches. The lower dimensions (in brackets) are in millimeters.

Figure 17:
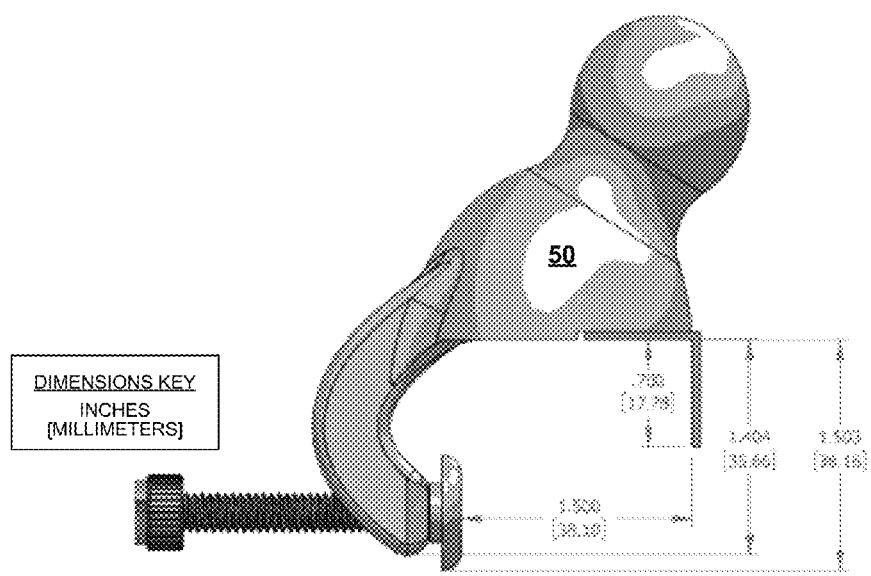
FIG. 17 is a diagram of a hand support device 50 showing dimensions from a side view when the fastening element is adjusted to allow for the maximum distance between the first and second contact surfaces.

FIG. 17 is a diagram of a hand support device 50 showing dimensions from a side view when the fastening element is adjusted to allow for the maximum distance between the first and second contact surfaces.

Figure 18:
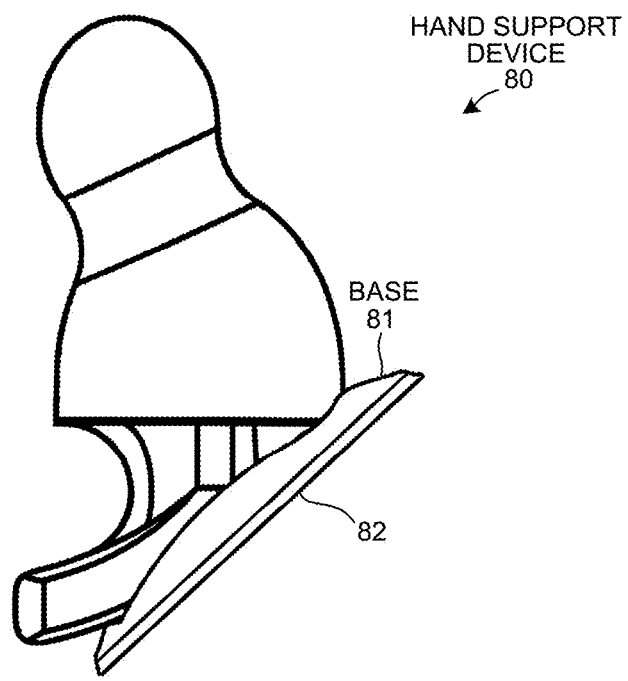
FIG. 18 is a diagram of another embodiment of a hand support device 80 having a base 81.

FIG. 18 is a diagram of another embodiment of a hand support device 80 having a base 81. The hand support device 80 has a substantially similar support portion as the hand support device 10 shown in FIG. 1, except the attachment portion of hand support device 80 does not have a clamping mechanism. The hand support device 80 has one and only one contact surface adapted to attach to a flat surface of a structure. The base 81 is part of the attachment portion. The bottom of base 81 includes a flat surface 82. The base 81 is mounted onto a flat surface of a structure so that the surface 82 contacts the flat surface of the structure. The structure may be a desk or a laptop. In the case of a laptop, the base 81 is mounted onto an area of the laptop within reaching range of the keys.

Figure 19:
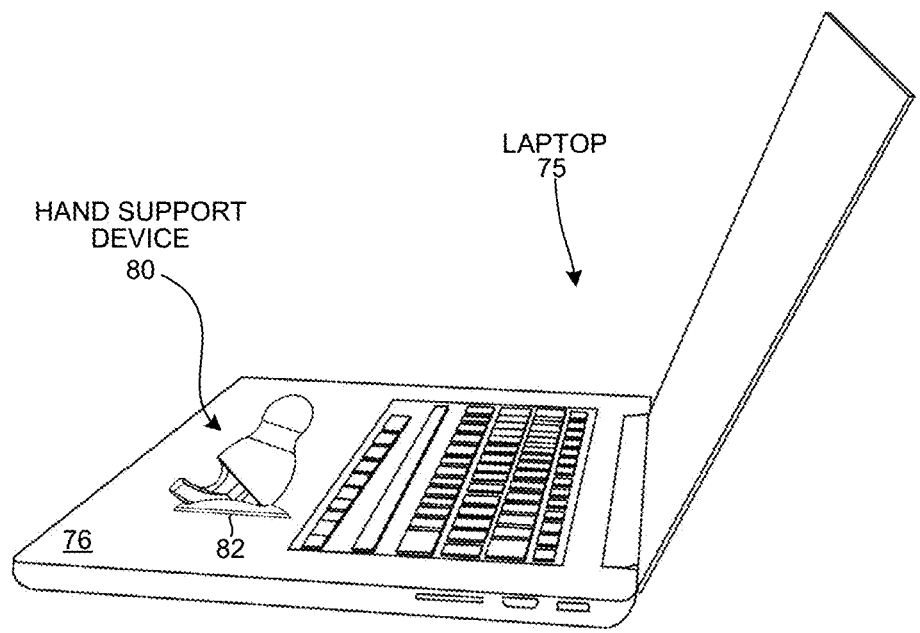
FIG. 19 is a diagram of a perspective view of the novel hand support device 80 attached to a laptop 75.

FIG. 19 is a diagram of a perspective view of the novel hand support device 80 attached to a laptop 75. The novel hand support device 80 contacts a single surface 76 of the laptop 75. The bottom surface 82 of base 81 is disposed above the surface 76. The novel hand support device 80 directly contacts the laptop. The attachment portion ensures that the hand support device 80 is held in place along the surface 76 of the laptop 75.

Figure 20:
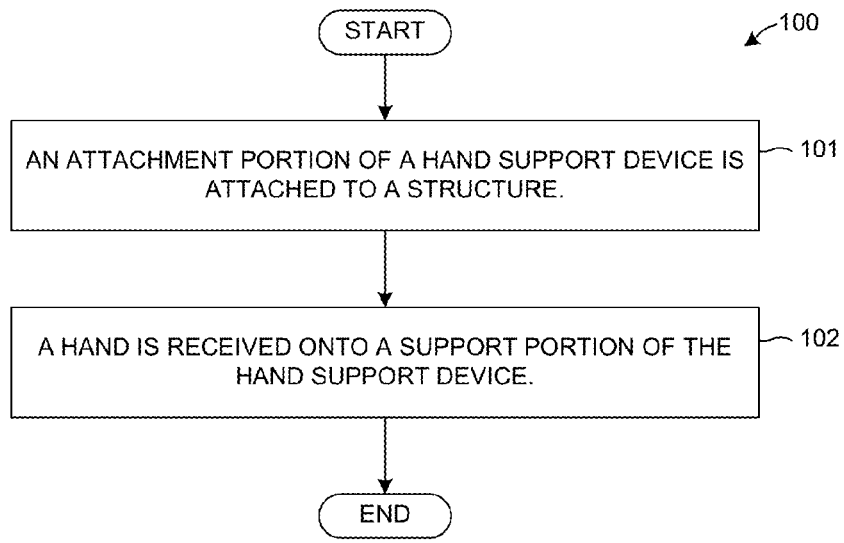
FIG. 20 is a diagram of a method 100 in accordance with one novel aspect.

FIG. 20 is a diagram of a method 100 in accordance with one novel aspect. In a first step (step 101), an attachment portion of a hand support device is attached to a structure. For example, in FIG. 8, the hand support device 10 is attached to the piano 36 by clamping the attachment portion 12 to the keyslip 35 by tightening the fastening element 24. The hand support device 10 contacts the structure along three surfaces of the structure. The tip 27 contacts an exterior surface of the keyslip 35. The ledge 22 contacts an interior surface of keyslip 35. The bottom surface 31 contacts an upper surface of the keyslip 35. In the example of FIG. 19, the hand support device 80 is placed above the laptop 75. The hand support device 80 contacts a single surface 76 of the structure.

In a second step (step 102), a hand is received onto a support portion of the hand support device. For example, in FIG. 10, the user 38 places his/her hand 37 above hand support device 10. The hand support device 10 is attached to the piano 36 by clamping mechanism of the attachment portion 12. The weight of the hand 37 above the head 20 causes a force to be applied to an area 39 of the palm shown in FIG. 11. By applying such a force to area 39 of the hand, the user 38 is able to play the piano 36 with augmented motor accuracy. In the example of FIG. 19, the user places his/her hand above hand support device 80. The hand support device 80 is attached to the laptop 75 by base 81 of the attachment portion. The weight of the hand above the head causes a force to be applied to an area 39 of the palm shown in FIG. 11. By applying such a force to area 39, the user is able to type on the laptop 75.

Figure 21:
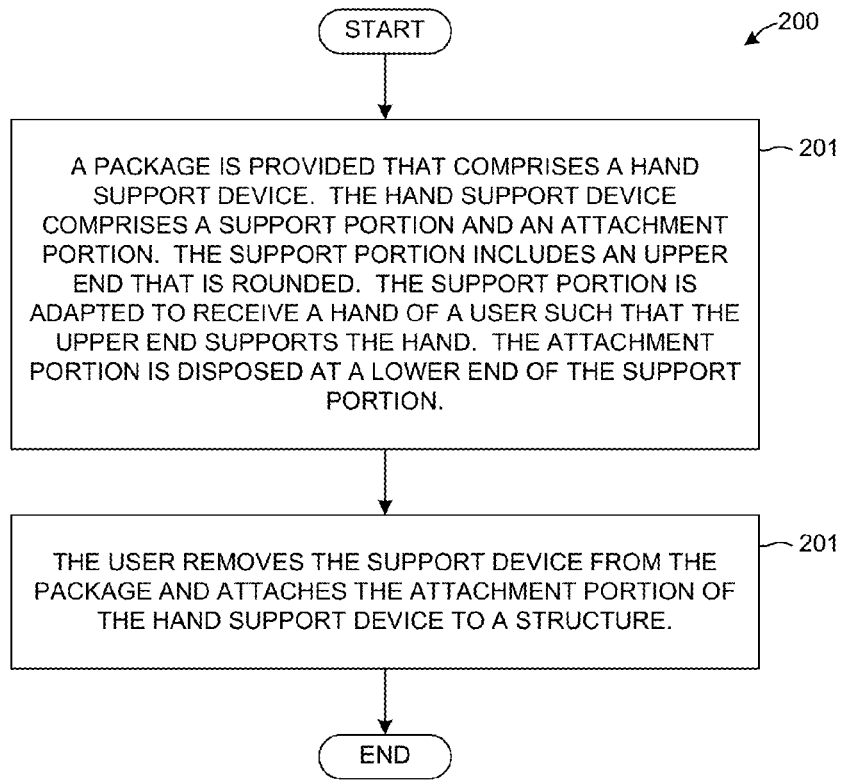
FIG. 21 is a diagram of a method 200 in accordance with a second novel aspect.

FIG. 21 is a diagram of a method 200 in accordance with a second novel aspect. In a first step (step 201), a package is provided that comprises a hand support device. The hand support device comprises a support portion and an attachment portion. The support portion includes an upper end that is rounded. The support portion is adapted to receive a hand of a user such that the upper end supports the hand. The attachment portion is disposed at a lower end of the support portion. For example, in FIG. 22, a package 211 is provided that comprises hand support device 10. The hand support device 10 has the support portion 11 and the attachment portion 12. The support portion 11 includes the upper end 13 that is rounded. The support portion 11 is adapted to receive a hand of a user such that the upper end 13 supports the hand. The attachment portion 12 is disposed at a lower end 14 of the support portion 11.

Figure 22:
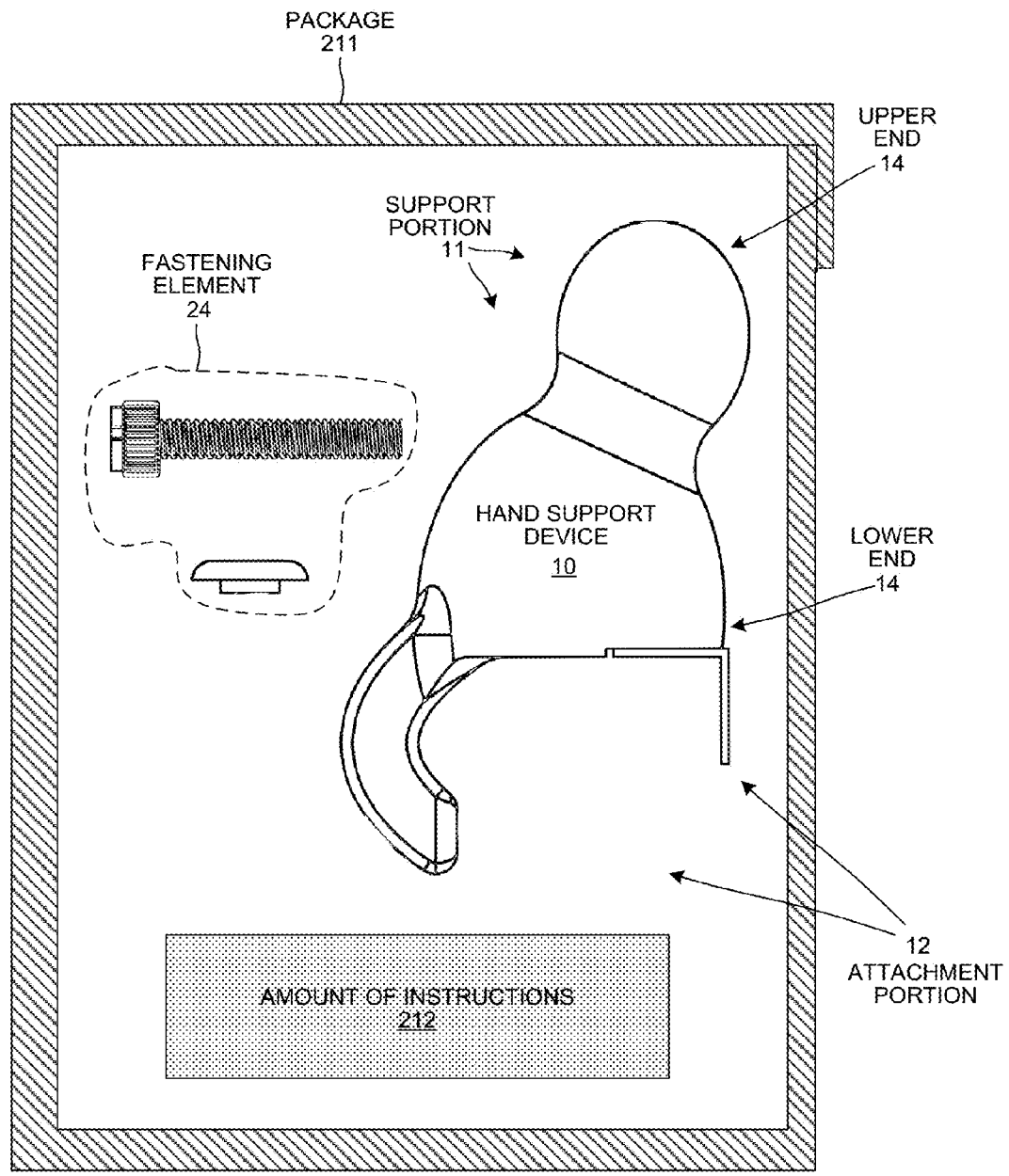
FIG. 22 is a diagram of a package 211 comprising hand support device 10.

In the example of FIG. 22, an amount of instructions 212 are provided in the package 211. The amount of instructions 212 instruct the user on how to attach the hand support device 10 to a structure and how to use the hand support device 10 to support the hand. In another embodiment, the instructions are provided digitally via a website. The user is given a URL that presents the instructions onto a display viewable by the user's network connected device. In yet another embodiment, the instructions are printed on the package 211. In yet another embodiment, the instructions are digitally provided via QR code that is included with the package 211. The user scans the QR code with a mobile communication handset thereby directing the user to digitally accessible instructions. In yet another embodiment, the instructions are sent to the user via an email communication.

In another example, a plurality of components is provided in a package. The plurality of components is assembleable into the novel hand support device. For example, the package comprises components that include a head, a body, a tail, a ledge, a fastening element, and screws. The package with components is provided to the user. Next, The user removes the components from the package. Next, the user attaches the plurality of components together to form the hand support device. Instructions on how to assemble the components to form the hand support device are optionally provided to the user.

Similar packaging and instructions are provided for the hand support device 80 that is shown in FIG. 18. A package (not illustrated) is provided that includes the hand support device 80 and an amount of instructions. The amount of instructions instruct a user to place surface 82 onto a laptop or desk. In another embodiment, the package 212 is a loosely packaged bag or pouch that includes the hand support device or components to assemble the hand support device.

Figure 23:
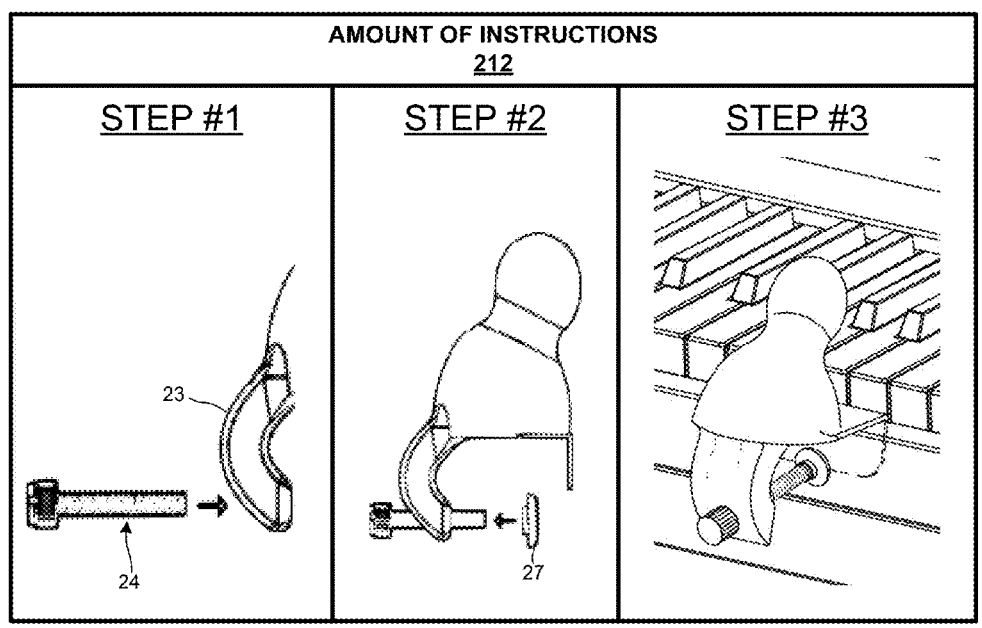
FIG. 23 is a diagram of the amount of instructions 212.

FIG. 23 is a diagram of the amount of instructions 212. Instructions 212 instruct a user to first insert threaded portion of fastening element 24 through hole of tail 23. Next, the instructions 212 instruct the user to attach tip 27 to the end of the threaded portion of fastening element 24. Next, the instructions 212 instruct the user to attach device 10 to the structure.

Although the present invention has been described in connection with certain specific embodiments for instructional purposes, the present invention is not limited thereto. For example, although the hand support device is shown as a solid, unitary structure, the hand support device may comprise a plurality of separable components. In addition, the hand support device 10 may be configured to have a non-adjustable clamping mechanism. For example, in another embodiment, two ledges extend downward from the base of the support portion. The keyslip of the piano is inserted between the two ledges such that the hand support is disposed above the keyslip. In this embodiment, the hand support device is not fixed in place and is slideable across the keyslip of the piano. This embodiment is preferred if the user desires to move his/her hands across the piano. However, in this embodiment, the distance between the first and second contact surfaces is not adjustable and is limited to pianos having keyslips of a particular thickness. Accordingly, various modifications, adaptations, and combinations of various features of the described embodiments can be practiced without departing from the scope of the invention as set forth in the claims.

What is claimed is:

1. An apparatus comprising:
    a support portion having an upper end and a lower end, wherein the upper end of the support portion comprises a head having a spheroidal shape that forms a rounded surface adapted to receive a hand, wherein the support portion extends from the lower end to the upper end along a first axis, and wherein the first axis forms an angle relative to a second axis disposed along the lower end of the support portion; and
    an attachment portion that is connected to the lower end of the support portion.

2. The apparatus of claim 1, wherein the first axis is a support axis, wherein the first axis is normal to a center of the rounded surface along the upper end of the support portion, and wherein the second axis is a base axis.

3. The apparatus of claim 1, wherein the angle between the first axis and the second axis is between twenty degrees and ninety degrees.

4. The apparatus of claim 1, wherein the attachment portion comprises a clamping mechanism having a first contact surface and a second contact surface, wherein the first contact surface is adapted to contact a first surface of a structure, and wherein the second contact surface is adapted to contact a second surface of the structure.

5. The apparatus of claim 4, wherein a distance between the first contact surface and the second contact surface is adjustable, and wherein the clamping mechanism comprises:
    a ledge, wherein the first contact surface is part of the ledge;
    a tail that forms a hole; and
    a fastening element that is adapted to extend through the hole, wherein the second contact surface is disposed at an end of the fastening element.

6. The apparatus of claim 1, wherein the attachment portion has a contact surface that is adapted to contact a single surface of the structure.

7. The apparatus of claim 1, wherein the support portion further comprises a body, wherein the head has a first extent, wherein the body portion has a second extent, and wherein the second extent is greater than or equal to the first extent.

8. The apparatus of claim 1, wherein the apparatus is symmetrical about a third axis, and wherein the support portion and at least part of the attachment portion are formed from a unitary structure.

9. A method comprising:
    attaching an attachment portion of a hand support device to a structure, wherein the hand support device has a support portion having a head and a body, wherein the head of the support portion has a globe shape and forms a rounded surface adapted to receive a palm of a hand, wherein a first axis extends from a lower surface of the body to the rounded surface of the head, and wherein the first axis forms an angle relative to a second axis disposed along the lower surface of the body.

10. The method of claim 9, wherein the first axis is a support axis, wherein the first axis is orthogonal to a center of the rounded surface along the head, and wherein the second axis is a base axis.

11. The method of claim 9, wherein the angle between the first axis and the second axis is between twenty degrees and ninety degrees.

12. The method of claim 9, wherein the attachment portion is attached to the lower surface of the body.

13. The method of claim 9, wherein the method further comprises:
    adjusting a distance between a first contact surface of the attachment portion and a second contact surface of the attachment portion, wherein the first contact surface is adapted to contact a first surface of the structure, and wherein the second contact surface is adapted to contact a second surface of the structure.

14. The method of claim 9, wherein the attachment portion contacts only one surface of the structure.

15. The method of claim 9, wherein the head has a first diameter, wherein the body has a second diameter, and wherein the second diameter is greater than or equal to the first diameter.

16. An apparatus comprising:
    a support portion having an upper end and a lower end, wherein the upper end of the support portion has a globular shape and forms a rounded surface adapted to receive a hand, wherein the support portion extends from the lower end to the upper end along a first axis, and wherein the first axis forms an angle relative to a second axis disposed along the lower end of the support portion; and
    a means for attaching the apparatus to a structure, wherein the means is connected to the support portion, and wherein the means contacts at least one surface of the structure.

17. The apparatus of claim 16, wherein the means is an attachment mechanism that includes a tail, a ledge, and a fastening element, wherein the attachment mechanism is disposed along the lower end of the support portion, wherein a surface of the ledge is adapted to contact a first surface of the structure, wherein the fastening element is adjustable along an axis parallel to the second axis, and wherein the fastening element is adapted to be adjusted such that an end portion of the fastening element contacts a second surface of the structure.

18. The apparatus of claim 17, wherein the means is a clamping mechanism that comprises:
    a ledge, wherein the first contact surface is part of the ledge;
    a tail that forms a hole; and a fastening element that is adapted to extend through the hole, wherein the second contact surface is disposed at an end of the fastening element.

19. The apparatus of claim 16, wherein the angle between the first axis and the second axis is between twenty degrees and ninety degrees.

20. The apparatus of claim 16, wherein the means is adapted to contact one and only one surface of the structure.

* * * * *